United States Patent
Yang

(10) Patent No.: US 6,413,214 B1
(45) Date of Patent: Jul. 2, 2002

(54) APPLANATING TONOMETERS

(76) Inventor: Paul S. Yang, 133 East Park, Old Harlow, Essex CM17 OSA (GB)

(*) Notice: Subject to any disclaimer, the term of this patent is extended or adjusted under 35 U.S.C. 154(b) by 0 days.

(21) Appl. No.: 09/486,071
(22) PCT Filed: Aug. 20, 1998
(86) PCT No.: PCT/GB98/02505
§ 371 (c)(1), (2), (4) Date: Feb. 24, 2000
(87) PCT Pub. No.: WO99/09882
PCT Pub. Date: Mar. 4, 1999

(30) Foreign Application Priority Data

Aug. 22, 1997 (GB) .............................. 9717894

(51) Int. Cl.$^7$ ................................. A61B 5/00
(52) U.S. Cl. ..................................... 600/405
(58) Field of Search ................. 600/398, 401, 600/405, 406

(56) References Cited

U.S. PATENT DOCUMENTS

| 4,995,393 A | 2/1991 | Katsuragi et al. |
| 5,070,875 A | 12/1991 | Falck et al. |
| 5,355,884 A | 10/1994 | Bennett |

FOREIGN PATENT DOCUMENTS

| DE | 862920 | 3/1961 |
| DE | 3421701 A1 | 12/1984 |
| DE | 4444459 C1 | 2/1996 |
| EP | 0418746 A | 3/1991 |
| EP | 0536574 A1 | 4/1993 |

Primary Examiner—Max Hindenburg

(57) ABSTRACT

There is provided a tonometer including an applanating element having a light-transmitting contact face engageable against the eye of a subject for projecting a light beam onto the eye and passing reflected light therefrom. There are also means responsive to the reflected illumination and means responsive to the force of engagement of the applanating element on the eye for obtaining data of changing values of reflected illumination and force as the element is applied to the eye. The contact face has an area larger than a predetermined area of engagement at which the applanting force is to be determined. The instant of applanation of the predetermined area is obtained by interpolation. The cornea is applanated over the contact face area, dependent upon the ratio of the predetermined and larger areas of applanation, in order to determine the force measured at the instant of applanation of the predetermined area. Preferably, means are provided for processing progressive measurements of the force and reflected illumination to derive a measure of acceleration of the applanating element at the moment of applanation, and preferably automatically correcting the applanating force measurement accordingly, in order to compensate for dynamic force components that may appear in the measurement of the force on the applanting element. The readings obtained can thereby be rendered independently, or at least less dependent, of any variations in the rate of application of the contact face against the cornea. In this way the use of the tonometer as a hand-held instrument can be facilitated without compromising the accuracy of measurement.

12 Claims, 4 Drawing Sheets

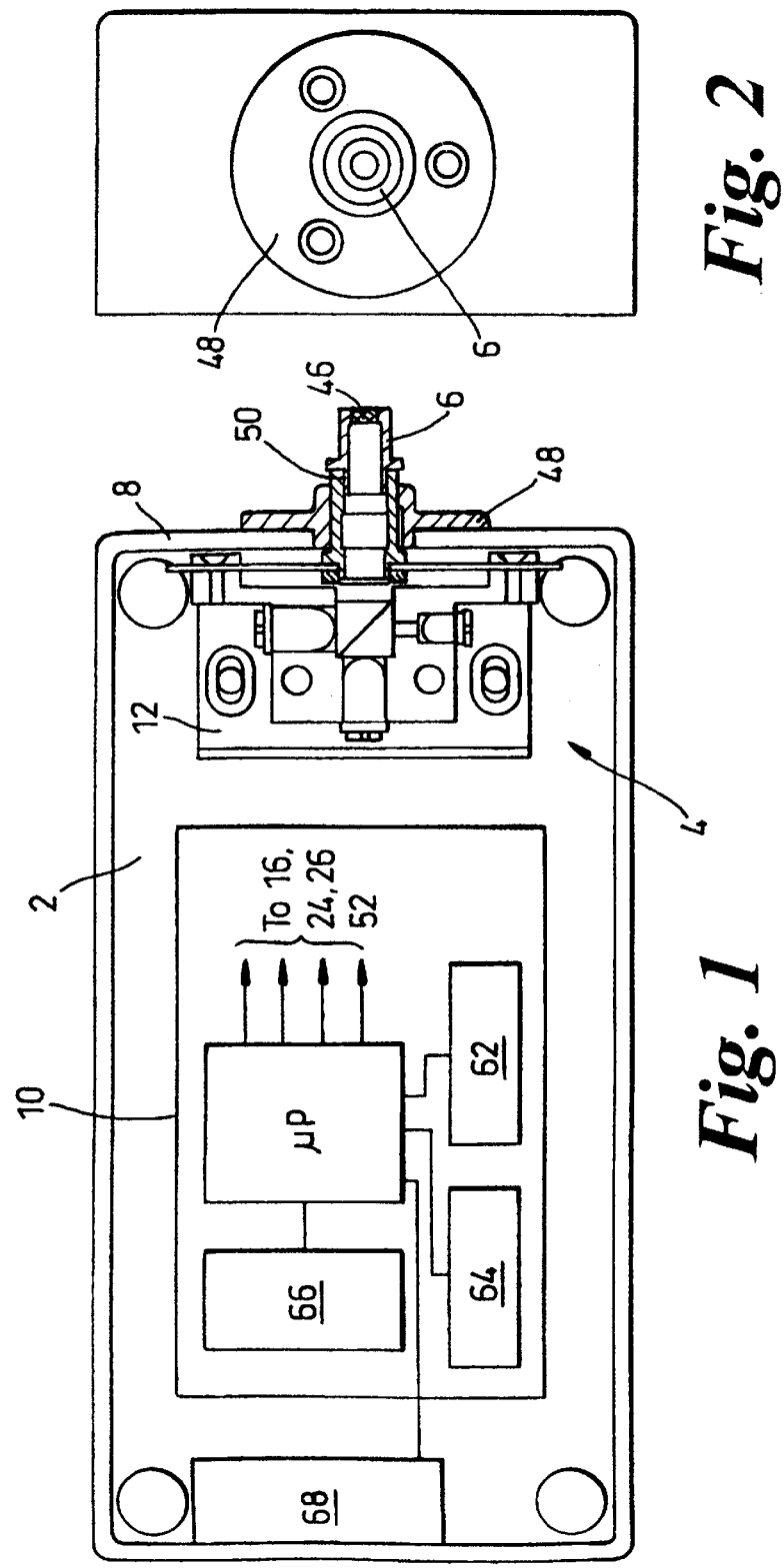

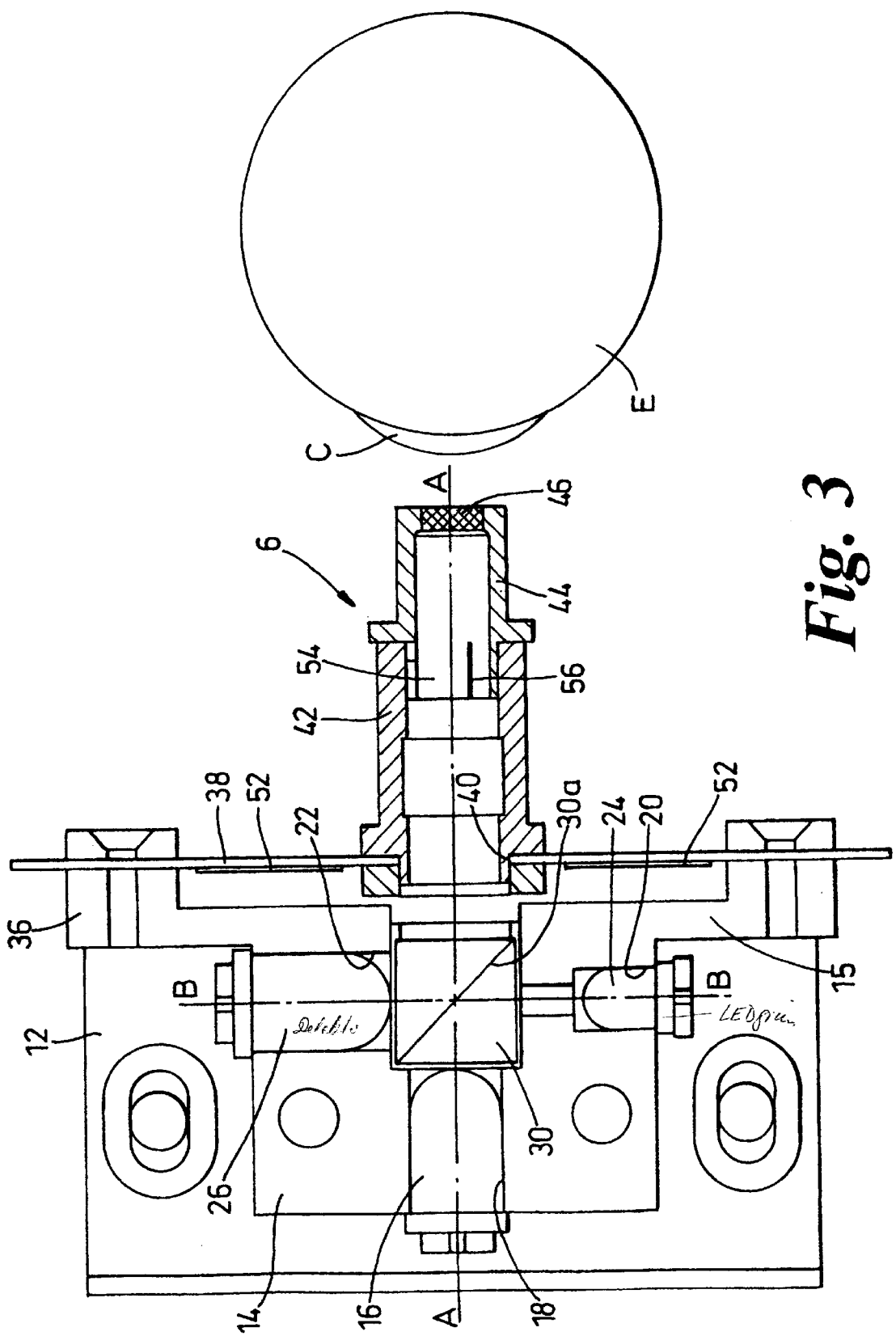

APPLANATING TONOMETERS

This application is the national phase under 35 U.S.C. § 371 of PCT International Application No. PCT/GB98/02505 which has an International filing date of Aug. 20, 1998, which designated the United States of America.

BACKGROUND OF THE INVENTION

1. Field of the Invention

This invention relates to applanating tonometers for the measurement of intraocular pressure (IOP).

2. Description of Related Art

Known applanating tonometers employ a transparent applanating element with a contact face through which light can be transmitted onto, and be reflected from, the eye of a subject in a manner which varies with the degree of applanation. The aim is to determine the force required to put the contact face in contact with the cornea of the eye to applanate a given area and so provide a measure of the IOP.

One example of such a tonometer is described in GB 862920, which is a version of the instrument known as the Goldman tonometer. In order to standardize the area of applanation and avoid the need for pre-calibration, which-brings its own problems as explained in that document, the eye is observed through an applanating element that comprises a split prism. When the element is applied against the eye, the area of applanation can be observed through the split prism as two semi-circular images displaced relative to each other by an amount determined by the parameters of the prism. As the force of applanation and the applanated area increases, the images increase in size and the object observed when the half images come together, are seen as a continuous S-shaped line, when the image diameter equals the displacement of the images. This dimension is standardized, for practical reasons, at 3.06 mm.

However, the images produced do not allow a precise and unambiguous determination of the coming together of the images. A degree of subjective judgement is needed and there can therefore be significant variations in the readings taken. The readings are also dependent on the skill of the user, because it is not easy to ensure that the applanating element is always applied squarely to the cornea. Any tilt of the contact face relative to the eye will introduce measurement errors.

It would therefore be desirable to provide an instrument that could be operated with less dependence on the user's skills and judgement in order to provide a more objective reading of intraocular pressure.

SUMMARY OF THE INVENTION

According to one aspect of the present invention, there is provided a tonometer comprising an applanating element having a light-transmitting contact face engageable against the eye of a subject for projecting a light beam onto the eye and passing reflected light therefrom. There are also means responsive to the reflected illumination and means responsive to the force of engagement of the applanating element on the eye for obtaining data of changing values of reflected illumination and force as the element is applied to the eye. The contact face has an area larger than a predetermined area of engagement at which the applanting force is to be determined. The instant of applanation of the predetermined area is obtained by interpolation. The cornea is applanated over the contact face area, dependent upon the ratio of the predetermined and larger areas of applanation, in order to determine the force measured at the instant of applanation of the predetermined area.

Preferably, means are provided for processing progressive measurements of the force and reflected illumination to derive a measure of acceleration of the applanating element at the moment of applanation, and preferably automatically correcting the applanating force measurement accordingly, in order to compensate for dynamic force components that may appear in the measurement of the force on the applanting element. The readings obtained can thereby be rendered independently, or at least less dependent, of any variations in the rate of application of the contact face against the cornea. In this way the use of the tonometer as a hand-held instrument can be facilitated without compromising the accuracy of measurement.

In a further aspect, the invention also provides a method of measuring intraocular pressure in which a contact face of an applanating element is applied against the eye of a subject and measurements are made that are indicative of both the degree of applanation and the force applied to the applanating element. The measurements are made while increasing the pressure of application until the contact face is fully applied against the eye to produce a predetermined lesser extent of applanation by the element by interpolation of the measurements of force.

According to another aspect of the invention, there is provided a tonometer comprising an applanating element having a contact face engageable against the eye of a subject and having means for determining the alignment of the contact face to the eye. The means comprising a light source directing a beam onto a beam-splitting element which transmits a first part of the beam onto a first reflecting element and reflects a second part of the beam onto a second reflecting element. Light from the first part of the beam is arranged to be reflected by the beam splitting element to the contact face and light from the second part of the beam being arranged to be transmitted through the beam-splitting element to the contact face. The positions of the images of the light from the first and second parts of the beam falling on the retina of the eye and are thereby dependent upon the relative alignment between an optical axis of the tonometer and the optical axis of the eye.

In such a tonometer, it can be arranged that the two reflecting elements are provided by front faces of a light-emitting device for producing an applanation measurement beam and a light-receiving device for reflected illumination from the eye of the measurement beam to derive a measure of the applanation pressure.

Conveniently, the elements can provide conjugate paths for the light transmitted for the light source to their respective reflecting surfaces. If the reflecting surfaces are located symmetrically to the optical axis of the tonometer, it can be arranged that by bringing the observed images into coincidence with each other will indicate that alignment has been achieved.

BRIEF DESCRIPTION OF THE DRAWINGS

One embodiment of the invention will be described by way of example with reference to the accompanying drawings, in which:

FIGS. 1 and 2 are plan and front views of an applanating tonometer according to the invention with the cover of its housing removed;

FIG. 3 is a plan view of the electro-optical unit of the instrument to a larger scale;

DETAILED DESCRIPTION OF PREFERRED EMBODIMENTS

Figure 4:
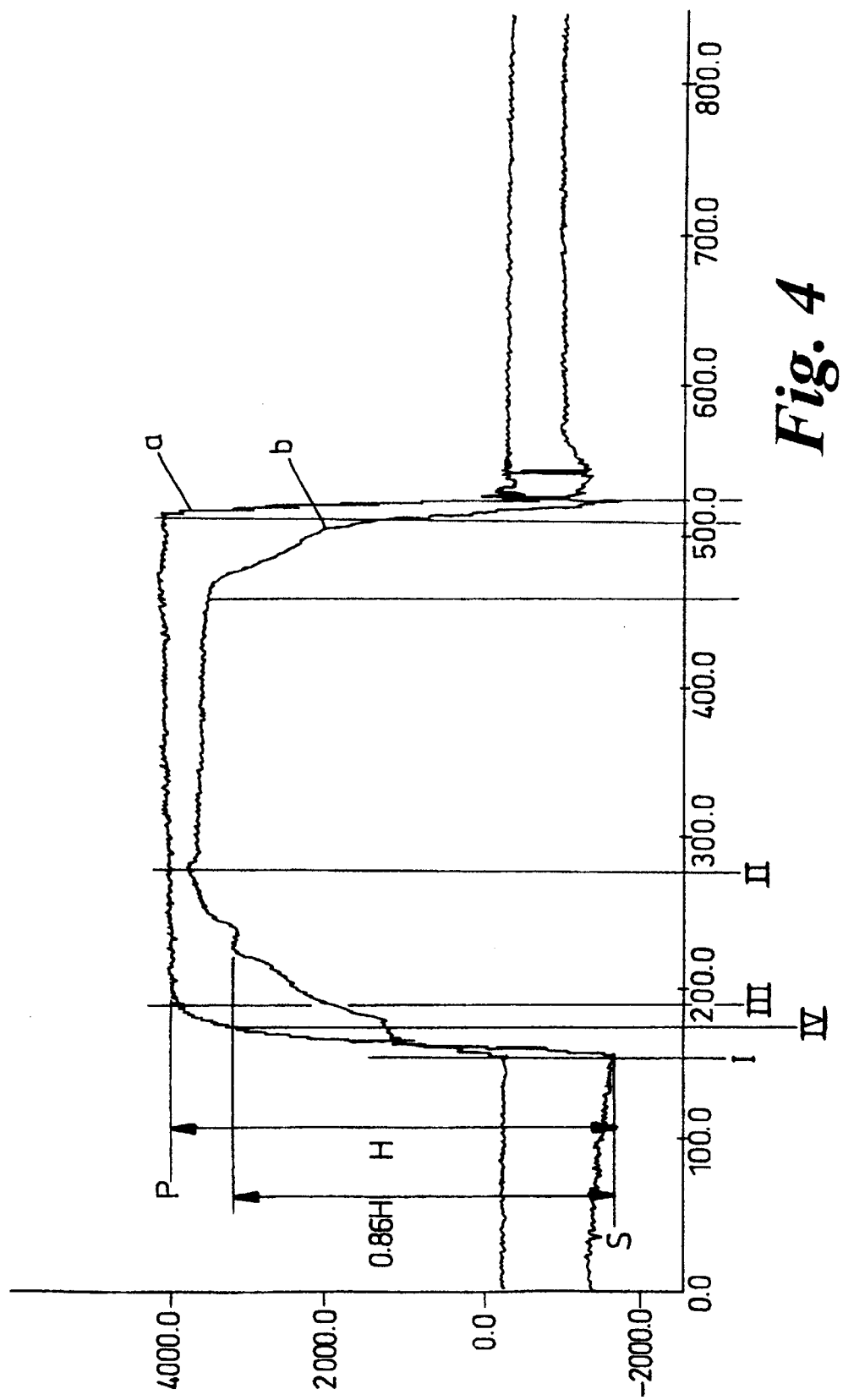
FIG. 4 is a graph illustrating the operation of the instrument of FIGS. 1–3.

Referring first to FIGS. 1 and 2, mounted in a housing 2 of the instrument, which can be held in the hand of the operator, is an electro-optical unit 4 comprising an applanating probe 6 projecting from the front wall 8 of the housing. A circuit board 10 in the housing carries a microprocessor $\mu$P connected to electrical elements of the unit 4 for evaluating the signals they produce.

The electro-optical unit 4 comprises a base plate 12 on which are secured a U-frame 14 (FIG. 3) and a front wall 15. In the central limb of the U-frame 14 an infra red emitter 16 is held in a bore 18, aligned on a main central optical axis A—A of the instrument. In coaxial bores 20,22 in the side limbs of the U-frame 14 and aligned on an optical axis B—B perpendicular to and intersecting the main optical axis A—A, are a green LED 24 and a photo-transistor 26. The preferred photo-transistor, Siemens SFH300FA-3, has a very narrow infra-red wavelength receiving hand and a black face which comprises a daylight filter. Located between the arms of the U-frame is a beam splitter 30 having a reflection plane 30a at 45° to both optical axes A—A and B—B, and meeting both axes at their intersection. The emitter 16 and phototransistor 26 are equidistant from that point of intersection.

Projections 36 at opposite ends of the front wall 15 support a resiliently, flexible beam 38 having central opening 40 in which the applanating probe 6 is secured. The probe 6 has a cylindrical body 42 aligned with the main optical axis A—A. The body 42 carries an applanating head 44 closed at its forward end by an optically flat window 46 providing the applanating surface to be applied to the cornea C of the eye E of a subject. The probe 6 is maintained in alignment with the optical axis A—A by a guide 48 (FIG. 1), secured to the front wall 8 of the housing, comprising a tubular portion 50 in which the cylindrical body 42 of the probe is a sliding fit. Fixed to the rear face of the beam 38 to each side of the probe are strain gauges 52 which respond to the beam deflection produced when the probe 6 glides in its guide 48.

For reasons of hygiene, the applanating head 44 is readily replaceable. It comprises a skirt 54 with three symmetrically spaced slits 56 to provide a degree of resilience so that it can be gripped frictionally by the body 42 and slid out when it is to be replaced.

In use, light from the infra red emitter 16 passing along the main optical axis A—A through the beam splitter 30 is directed through the window 46 onto the cornea C of the subject. Part of the light reflected back from the cornea through the window 46 is reflected by the beam splitter 30 onto the photo-transistor 26 to generate a signal that is dependent upon the intensity of the reflected light. No reflection will occur where the window is in contact with the cornea, so the photo-transistor signal is dependent upon the degree of applanation of the cornea by the window. Green light from the LED 24 is also transmitted through the beam splitter 30 to the phototransistor 26 but the light is outside the receiving band of that element so that its output is not affected. The LED output serves solely to assist alignment of the instrument, as will be described further below.

When the applanating probe 6 is forced into contact with the cornea, the flexible beam 38 will be deflected. The strain gauges 52 mounted on the beam are connected into a bridge circuit (not shown) on the circuit board 10 to measure the deflection in order to obtain an indication of the force applied to the beam. At the initial stage of contact, when the force is small, there will only be a small interface formed between the window 46 and the cornea C. As the force and the area of contact increase, so the amount of reflected light falls. While the instrument is applied to the eye the signals from the photo-transistor 26 and the strain gauges 52 are inputted to a memory store 62 (FIG. 1) connected to the micro-processor $\mu$P so that data can be held of the increasing applanating force and the reducing amount of reflected light related to a common time base.

The graph of FIG. 4 shows, against the time base, traces a and b respectively of the optical signal and force data as the probe is applied to the eye and then withdrawn again. For convenience the optical trace a is shown inverted and it indicates how, as the probe is applied with increasing force, from an initial value S, the light is reflected from the cornea drops with increasing area of contact, and then increases again when the force is removed. Once the entire area of the window is covered the reflection signal remains constant at a plateau value P, even though FIG. 4 shows the force trace b continuing to increase as the probe may be pressed further against the eye to ensure full contact has been made. Similarly, as the probe is withdrawn, only after the deflection force has decreased sufficiently for the window to begin to be uncovered, does the optical reflection signal change.

As described earlier, in conventional applanating tonometers, such as the Goldman tonometer, the aim is to measure the force at which the cornea is flattened over a predetermined area of 3.06 mm. The diameter of the probe window in the present instrument is made slightly larger at 3.3 mm, although the instrument is intended to provide a force reading for the standard 3.06 mm diameter value, for a reason that will now be explained.

Referring to the graph of FIG. 4, as can be seen from the optical trace, the signal changes rapidly as the applanating pressure of the probe is increased, but this change slows progressively in a transition region immediately before the window 46 completely covers the cornea and a plateau value is reached. It is not possible, therefore, to identify precisely the point at which the plateau value is first reached. Furthermore, in these conditions any noise in the signal represents a source of further uncertainty.

However, it will be seen that the plateau value itself is very clearly indicated and it is known that this corresponds to a state of full contact between the window 46 and the cornea C. By taking the ratio of the squares of the actual and standard window diameters, in this example giving the value 0.86, it is therefore possible to identify relatively accurately a point on the optical trace where the change of reflectivity has reached 0.86 of the change to the plateau value. This represents the point at which there is contact with an area of 3.06 mm diameter and the force value at the same time instant therefore indicates the strain gauge response when the standard area of applanation has been achieved by the probe window.

It may be noted that this procedure gives a reading which is not dependent upon the absolute values of the initial optical signal before contact with the cornea nor the plateau signal. Therefore, although the reflectivity of the eyes of different subjects can vary the derivation of the required signal value will not be affected as this is simply an objective measure of the overall change of signal in the ratio of the actual window size to the chosen standard window size.

A program store 64 (FIG. 1) in conjunction with the microprocessor AP executes the measurement program described. FIG. 1 also shows a power supply 6G for the electrical circuitry and read-out device 68 for the values obtained.

The manner in which the data of the traces is evaluated in the microprocessor, will be described with reference to FIG. 5. The stored data is first smoothed and the start point I (FIG. 4) of the optical trace, at which the applanating element makes initial contact with the subject's eye is determined. The corresponding optical signal value S is extracted and also the plateau value P of the optical trace at an instant II some time after the transition (indicated at III) to the steady state optical signal. The difference between the optical signals at I and II is then evaluated and provides a measure of the total change of optical signal during the applanation of the cornea to the full 3.3 mm diameter of the window, i.e. the dimension H. Taking then a rise of optical signal of 0.86H from the value at the start point I, a reference point is obtained on the optical trace which identifies the time instant IV, corresponding to the instant of contact with a standard 3.06 mm diameter window area. The value of the force trace at time instant IV therefore indicates the force measured by the strain gauges when the applanation has reached the standard 3.06 mm diameter area, and that value can be displayed on the read-out device 68.

Figure 5:
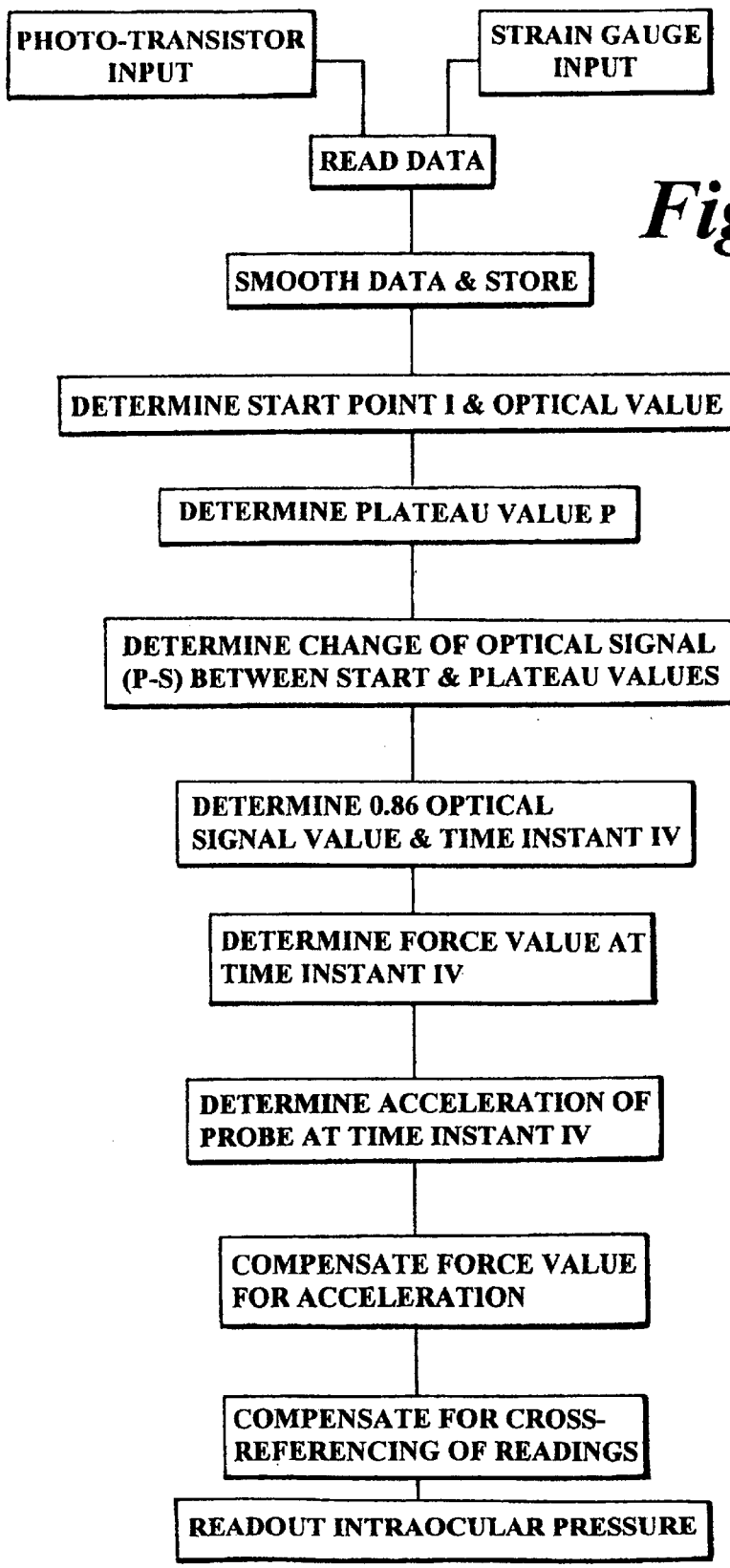
FIG. 5 is a flow diagram illustrating the sequence of operations in performing a reading.

FIG. 5 illustrates some further processing of the force value obtained to increase the accuracy of measurement. Because the probe is still moving forwards at the time instant IV, the strain gauge signal can also include a dynamic component from any acceleration or deceleration of the probe. It is therefore desirable to adjust the signal value to compensate for this effect. The time taken for the movement from initial contact to applanation of the standard 3.06 mm diameter is given by the interval between the points I and IV on the optical trace. the distance moved can be calculated with sufficient accuracy by assuming a spherical radius of 7.9 mm, for the cornea, to give a value of 0.15 mm. From the optical trace it is then possible to determine what, if any, acceleration or deceleration is occurring at the time instant IV. The mass acted upon is sufficiently closely represented by the mass of the slidable probe, so on the basis of this data the microprocessor is able to calculate the acceleration force and compensate the strain gauge signal accordingly to adjust the value displayed on the read-out device.

When measuring the IOP of a subject, the value obtained will vary, for example due to variations in instantaneous blood pressure. It is desirable, therefore, to cross-reference a series of readings in order to obtain a final read-out that is at least partially compensated for such effects. The preferred method of cross-referencing uses five successive readings, but those giving the highest and lowest IOP values are discarded. From the remaining three readings the change of optical signal, i.e. the values H, are averaged. Larger H values are found to give larger force measurements and the force values are adjusted to accord with the mean H value before they are averaged for the read-out of IOP on the read-out device 68.

The instrument described can be arranged as a bench-mounted instrument with a mechanical drive for advancing the probe to give a uniform operating sequence, in which case any correction applied for acceleration force can be a constant value.

If the apparatus is in the form of a hand-held instrument, the operating program is preferably adapted to detect abnormal modes of operation that may then occur. In particular, the operator may stop moving the probe forwards too soon to establish a true plateau value or the contact with the eye may not be maintained for a long enough period. If either fault is detected, the micro-processor can be programmed to abort the following sequence of operations and display an invalid reading message.

A possible source of error arises in the use of an applanating tonometer if the contact face of the probe is tilted in relation to the eye. The green light emitted from LED 24 is used to assist alignment of the instrument with the eye and so avoid any such error. Some of the light emission from the LED passes through the reflection plane 30a of the beam splitter to impinge on the photo transistor 26 which is a conventional device with a generally hemispherical reflective front face, so that some light is returned to the beam splitter where a part is reflected at the plane 30a to pass through the probe 6 onto the eye. Another part of the incident light from the LED 24 is reflected by the beam splitter 10 onto the infra red emitter 18 which similarly has a generally hemispherical reflective front face. Part of the light reflected from the emitter front face will thus be transmitted to the eye is through the reflection plane of the beam splitter and the probe 6.

The eye of the subject therefore receives green light reflected on conjugate paths from both the infra red emitter and, to a lesser extent because of its black surface, the photo-transistor. In each case, the image projected by the curved reflecting faces has a central brighter zone merging into a dimmer halo. If the axis of the eye and the axis of the probe are in alignment, the images are superimposed directly onto each other and a central circular bright spot will be seen by the subject.

If the axes are tilted or offset relative to each other, there will be a change in the images seen because the reflected light distribution reaching the eye of the subject is no longer symmetrical about a central axis. The subject will therefore be able to indicate that the probe is correctly aligned both before and during operation of the instrument by observing when a symmetrical brighter zone lies in the center of the surrounding halo.

It will be understood that this method of monitoring alignment can be used independently of whether the method of measuring IOP described above is used or not.

It will also be understood that the apparatus described can be modified in many ways within the scope of the invention. For example, although the frame 14 holding the optical elements 16,24,26,30 is shown secured rigidly to the base plate 12, it may be preferred to secure these elements to the probe body 42, directly or indirectly, so that they are fixed in relation to the optical element of the applanating head 44.

What is claimed is:

1. A tonometer comprising:
   an applanating element having a light-transmitting contact face engageable against the eye of a subject for projecting a light beam onto the eye and passing reflected light therefrom,
   means responsive to the reflected illumination and means responsive to the force of engagement of the applanating element on the eye for obtaining data of changing values of reflected illumination and force as the element is applied to the eye, said contact face having an area larger than a predetermined standard area of engagement at which the applanating force is to be determined, the instant of applanation of said predetermined standard area being obtained by interpolation from a signal obtained from the reflected illumination when the cornea is applanated over the contact face area, the instant of applanation being dependent upon the ratio of said predetermined standard and larger areas of applanation, in order to determine the force measured at said instant of applanation of the predetermined standard area.

2. A tonometer according to claim 1 comprising means for applying a correction to said determined force for a dynamic force component acting between the applanating element and the eye at said instant of applanation.

3. A tonometer according to claim 2 wherein means are provided for processing progressive measurements of the force and reflected illumination to derive a measure of the dynamic force component at said instant of applanation.

4. A tonometer according to claim 1 wherein the applanating element is guided for rectilinear displacement on a resilient mounting and the applanating force is derived from a measurement of the deflection of the mounting when said element is applied against the eye.

5. A tonometer according to claim 4 wherein a beam splitting element is located in a path of light beam transmission from an illumination device to the eye, the reflected light beam returned from the eye through the beam splitting element being directed onto a detecting device forming the means responsive to the reflected illumination, the beam associated with one said device passing directly through the beam splitter and the beam associated with the other said device being reflected by the beam splitter.

6. A tonometer according to claim 5 wherein the illumination device is arranged to transmit the incident light beam along an axis extending in the direction of displacement of the applanating element.

7. A tonometer according to claim 5 comprising a monitoring light source arranged to direct light through the beam splitter onto respective front faces of the illumination and detection devices for reflection therefrom onto the eye of the subject, whereby the pattern of reflected light from said source observed by the subject will vary in dependence upon the alignment of the axis of the eye of the subject with the axis of the applanating element.

8. A tonometer according to claim 7 wherein said reflecting front faces of the illumination and detection devices are each rotationally symmetrical about an optical axis of the respective device, whereby misalignment of said axes is observable as a loss of symmetry in the pattern of reflected illumination.

9. A tonometer according to claim 2, wherein the applanating element is guided for rectilinear displacement on a resilient mounting and the applanating force is derived from a measurement of the deflection of the mounting when said element is applied against the eye.

10. A tonometer according to claim 3, wherein the applanating element is guided for rectilinear displacement on a resilient mounting and the applanating force is derived from a measurement of the deflection of the mounting when said element is applied against the eye.

11. A tonometer according to claim 6 comprising a monitoring light source arranged to direct light through the beam splitter onto respective front faces of the illumination and detection devices for reflection therefrom onto the eye of the subject, whereby the pattern of reflected light from said source observed by the subject will vary in dependence upon the alignment of the axis of the eye of the subject with the axis of the applanating element.

12. A method according to claim 9, wherein the alignment of the optical axis of the eye of the subject with a central axis of the applanating element is monitored by directing light from a monitoring light source in the tonometer onto respective mutually perpendicular reflecting surfaces to follow conjugate paths to said central axis, so that the pattern of the monitoring illumination observed by the subject varies depending upon whether there is misalignment of said axis.

* * * * *